United States Patent [19]

Dyer et al.

[11] Patent Number: 4,637,830
[45] Date of Patent: Jan. 20, 1987

[54] HERBICIDAL CONCENTRATES

[75] Inventors: Ross M. W. Dyer, Harston; Edward Nowak, Histon, both of England

[73] Assignee: Ciba-Geigy Corporation, Ardsley, N.Y.

[21] Appl. No.: 669,413

[22] Filed: Nov. 8, 1984

Related U.S. Application Data

[63] Continuation-in-part of Ser. No. 368,497, Apr. 15, 1982, abandoned.

[30] Foreign Application Priority Data

Apr. 24, 1981 [GB] United Kingdom ................. 8112773

[51] Int. Cl.$^4$ ...................... A01N 37/34; A01N 25/00
[52] U.S. Cl. ........................................ 71/105; 71/115; 71/116; 71/117; 71/DIG. 1
[58] Field of Search ................. 71/105, 116, 117, 115, 71/DIG. 1

[56] References Cited

U.S. PATENT DOCUMENTS

| 3,813,237 | 5/1974 | Fischer | 71/117 |
| 3,929,452 | 12/1975 | Kimura et al. | 71/116 |
| 4,332,613 | 6/1982 | Esposito | 71/116 |

FOREIGN PATENT DOCUMENTS

| 1058609 | 2/1967 | United Kingdom . |
| 1067033 | 4/1967 | United Kingdom . |
| 1067031 | 4/1967 | United Kingdom . |
| 1067034 | 4/1967 | United Kingdom . |
| 1097713 | 1/1968 | United Kingdom . |
| 1097712 | 1/1968 | United Kingdom . |

Primary Examiner—Catherine L. Mills
Attorney, Agent, or Firm—Edward McC. Roberts; Bruce M. Collins

[57] ABSTRACT

Aqueous herbicidal concentrates of the normally water insoluble alkanoic acid esters of ioxynil and bromoxynil are prepared by dissolving the esters in an aqueous solution of at least a threefold excess of a salt of herbicidal chlorobenzoic or chlorophenoxyalkanoic acids.

10 Claims, No Drawings

HERBICIDAL CONCENTRATES

CROSS REFERENCE

This is a continuation-in-part of Ser. No. 368,497 filed Apr. 15, 1982, now abandoned.

DETAILED DESCRIPTION

The present invention pertains to herbicidal compositions, specifically concentrated formulations of two or more herbicides.

It is a common practice to apply two or more herbicides simultaneously to combat a broader spectrum of weeds than would be achieved with either herbicide alone. It is highly desirable for this practice to provide a single concentrate formulation of such combinations which can be simply diluted at the location of the herbicide application. If the two herbicides can be formulated in the same medium, the formulation of such mixtures in concentrated form generally presents no problems. It is desirable, of course, when the two herbicides can be formulated in the same medium that the formulation medium be aqueous. This is not always possible, however, since one or both of the herbicides may have insufficient water solubility to permit the preparation of the desired concentrated formulation. In such cases the formulation generally will have to take the form of an emulsifiable concentrate utilizing organic solvents, which solvents increase cost as well as user and manufacturing hazards, or a wettable powder which is difficult to handle and has user and manufacturing hazards due to dust.

If the two components have different formulation requirements, however, that is if one is hydrophilic and one is lipophilic, it is necessary to utilize a different formulation for each and then to mix the two just prior to use, as in a spray tank. This in turn requires the storage and transportation of separate containers with appropriate measurement from both, not only adding to handling time and space requirements but also creating the opportunity for measuring errors and incompatibility.

Two classes of herbicides for which the desirability of combined application has been long recognized are (i) hydroxybenzonitrile derivatives and (ii) chlorophenyl carboxylic acid derivatives such as derivatives of chlorobenzoic acids and chlorophenoxyalkanoic acids. See, e.g. British Pat. No. 1,097,713.

The latter group, which may be typified by such compounds as (2,4-dichlorophenoxy)acetic acid (2,4-D) and ±2-(4-chloro-2-methylphenoxy)propionic acid (Mecoprop), are generally formulated in the form of either (i) alkali metal or amine salts which are amenable to aqueous formulations or (ii) esters such as isooctyl 2-(4-chloro-2-methylphenoxy)propionate which are formulated in organic solvents as emulsifiable concentrates. The latter esters, however, have undesirably high volatility as compared to the salts which can result in vapor drift to adjacent fields with consequent crop damage. Hence, if crop safety is to be maintained, aqueous formulation are preferred for this class of herbicides.

The former class of herbicides, the hydroxybenzonitriles, may be typified by 2,6-diiodo-4-cyanophenol (ioxynil) and 2,6-dibromo-4-cyanophenol (bromoxynil). The combination of this class of herbicides with the chlorophenyl carboxylic acids, discussed above, initially either utilized the acidic nature of the phenol by providing aqueous solutions of the alkali metal, ammonium and amine salts of both components, or employed non-water soluble esters in self emulsifiable concentrates in organic solvents. See e.g. British Pat. No. 1,097,713. It has been recognized, however, that aqueous concentrates employing the salt forms of ioxynil and bromoxynil give rise to difficulties because the salts are not sufficiently soluble in water. See e.g. British Pat. Nos. 1,058,609 and 1,097,712. Various proposals to overcome this problem, such as the use of glucamine salts or the utilization of mixed solvents consisting of water and an organic solvent, have been suggested. Nevertheless bromoxynil and ioxynil are generally sold and used as their alkanoic acid esters, typically the octanoic acid ester, which being lipophilic must be formulated in hydrocarbon solvents. See e.g. U.S. Pat. No. 4,337,613. While such esters have advantageous properties as compared to the free phenol or salts thereof, notably greater biological activity and greater "rain fastness", the required hydrocarbon formulation suffers from the disadvantages discussed above.

Current practice for the simultaneous application of these two types of herbicides thus is to dilute and mix together in the spray tank an emulsifiable concentrate of the bromoxynil or ioxynil ester in an organic solvent with an aqueous concentrate of the chlorophenoxyalkanoic acid salt solution, or alternatively, as noted above, to have "all salt" or "all ester" formulations. Until now the lipophilic bromoxymil esters and the hydrophilic chlorophenyl carboxylic acid salts have not been compatible for formulation together in a single aqueous concentrate.

The present invention is based on the discovery that the above problems associated with known herbicidal compositions can be overcome by the use of a mixed aqueous salt/ester formulation. This combination of active ingredients provides a product which has all the advantages of bromoxynil and ioxynil esters together with the low volatility of a salt of a chlorophenyl carboxylic acid in aqueous media.

Specifically the invention pertains to an aqueous liquid concentrate of at least two herbicides comprising
(a) a first herbicide of low water solubility which herbicide is selected from the group consisting of
   (i) a 2,6-diiodo-4-cyanophenyl alkanoate having up to 12 carbon atoms in the alkanoate group;
   (ii) a 2,6-dibromo-4-cyanophenyl alkanoate having up to 12 carbon atoms in the alkanoate group; and
   (iii) a mixture of (i) and (ii);
the first herbicide being present in the concentrate in an amount which is herbicidally effective and at a concentration which exceeds the normal solubility of the herbicide in water, but nevertheless being fully dissolved in
(b) an aqueous solution of at least a threefold excess, relative to the amount by weight of the first herbicide, of a second herbicide so as to produce a clear, stable, homogeneous concentrate of the first and second herbicides.

The second herbicide is a salt of a carboxylic acid in which
   (i) the cation is selected from the group consisting of the sodium, potassium, ammonia, dimethylamine, diethylamine, monoethanolamine, diethanolamine, triethanolamine and morpholine cations, and
   (ii) the anion is selected from the group consisting of the 2,3,6-trichlorobenzoic acid; 3,6-dichloro-2-methoxybenzoic acid; 2,4-dichlorophenoxyacetic acid; 2,4,5-trichlorophenoxyacetic acid; 2-methyl-4-chlorophenoxyacetic acid; 2-(2-methyl-4-chlorophenoxy)propionic acid; 2-(2,4-dichlorophenoxy)-propionic acid; 2-(2,4,5-trichlorophenoxy)propionic acid; 4-(2-methyl-4-chlorophenoxy)butyric acid; and 4-(2,4-dichlorophenoxy)butyric acid anions.

The alkanoate portion of the first herbicide will contain from 1 to 12 carbon atoms, preferably 2 to 8 carbon atoms, as for example acetoxy, propionyloxy, butyryloxy, pentanoyloxy, octanoyloxy, or the like. Such alkanoates are lipophilic in nature and as such have a significantly lower solubility in water than the free phenols or even the salts of such phenols. Hence while not ordinarily soluble in water, surprisingly they are soluble in aqueous solutions of a large excess of the above defined second herbicide which, as noted, is a salt of carboxylic acid.

The concentration of the second herbicide is important since the higher its concentration, the greater is its solubilizing effect upon the first herbicide which, as noted, normally is of very low solubility in water. The resulting ratio of the second herbicide to the first herbicide will be at least 3:1 and preferably from 4:1 to 12:1 by weight respectively, expressed as the active moiety viz the free phenol or carboxylic acid, respectively.

The solubilizing effect of the second herbicide also will be dependent on chemical structure. That effect is increased with the presence and increasing length of the alkanoic acid chain and decreased by increasing the number of halogen atoms on the phenyl ring. However, the latter effect is less pronounced than the former effect. The following series, for example, illustrates typical acids in order of decreasing solubilizing effect of their salts:

4-(4-chloro-2-methylphenoxy)butyric acid (MCPB),
4-(2,4-dichlorophenoxy)butyric acid (2,4-DB),
($\pm$)-2-(4-chloro-2-methylphenoxy)propionic acid (Mecoprop),
4-chloro-2-methylphenoxyacetic acid (MCPA),
($\pm$)-2-(2,4-dichlorophenoxy)propionic acid (2,4-DP),
2,4-dichlorophenoxyacetic acid (2,4-D),
2,4,5-trichlorophenoxyacetic acid (2,4,5-T),
($\pm$)-2-(2,4,5-trichlorophenoxy)propionic acid (Fenoprop),
2,3,6-trichlorobenzoic acid (2,3,6-TBA).

The present formulations demonstrate the following, commercially important, characteristics:
(1) They are homogeneous products which do not separate or crystallize under normal storage conditions.
(2) They readily form a stable dispersion or solution when added to water in a spray tank, as can be demonstrated in the laboratory using CIPAC Test method Number MT 36 (an official test of the Collaborative International Pesticides Analytical Committee).
(3) They are physicochemically stable, as can be seen by storing the product in its finished pack for its intended shelf life and re-examining properties 1 and 2, above as well as measuring any change in active ingredient content.
(4) They have satisfactory low temperature stability and will not crystallize at low temperatures, as can be demonstrated in the laboratory according to CIPAC Test Method Number MT 39.

The present concentrate is prepared most simply by dissolving an appropriate amount of the second herbicide (which is manufactured as a solid) in an aqueous solution of the salt of the first herbicide (which is conventionally manufactured as an aqueous solution of its salt) with agitation until a clear formulation is obtained, optionally with heat to facilitate dissolution. Such produces a clear, stable, homogeneous formulation.

Certain additional components optionally can be present.

Firstly, a minor amount, from 1 to 10% w/v, Preferably 2 to 5%, of an aromatic solvent effectively inhibits crystallization from the composition at low temperatures. Suitable solvents include commercial solvents such as Solvesso 200 (Esso) Shellsol R (Shell), heavy naphtha (Carless Solvents, Inc.), xylene, di-(n-butyl)phthalate, 1,2-dichlorobenzene and the like.

Secondly, since the formulations tend to have an alkaline pH, the first herbicides, which are esters, can be hydrolyzed into the parent phenols and alkanoic acids. To reduce such alkaline hydrolysis desirably an acid is added in an amount sufficient to reduce the final pH to a value in the range of 7 to 8. Common organic acids, such as xylene sulphonic acid, citric acid and acetic acid and the inorganic acid nitric acid have been found to be suitable for this purpose. Apart from nitric acid, however, most inorganic acids are unsuitable.

The compositions also may contain a minor amount of a surface active agent, e.g. from 0 to 10% by weight which need only be of non-ionic character such as an alcohol ethoxylate or an ethylene oxide-propylene oxide polymer, although an anionic surface active agent may be used, if desired. Such a surface active agent, however, is not required in order to achieve a clear, stable, homogeneous formulation.

When one or more such components are present, they will be added during or after formulations. Surface active agents can be added to the solution of the second herbicide and any acid then added to buffer the same to a steady pH of about 7.5 prior to addition of the first herbicide. When the first herbicide has been dissolved, any co-solvent then is added.

Relative to the previously known "all salt" or "all ester" formulations, the compositions of the present invention have a number of advantages.

Firstly, the esters and salt are formulated as a single product. As noted above, currently farmers have to mix the ester as an emulsifiable concentrate with a chlorophenyl carboxylic acid salt solution in the spray tank in order to achieve the mixture of active ingredients. Hence handling time is reduced, as is the possibility of measuring errors. The use of a single pack, of course, is more convenient. Problems associated with the physical incompatability of tank mixes also are avoided.

Secondly, the main solvent used is water so that the resulting composition has a high flash point compared to oil based formulations containing esters and, as a consequence, presents less hazard to the manufacturer and user.

Thirdly, the ioxynil and bromoxynil esters are more biologically active and "rain fast" than their equivalent salt derivatives.

Finally, because of its desirable volatility properties, the composition cause little or no damage to adjacent crops through vapor drift.

The compositions can be used to control the growth of broad-leafed weeds such as Bugle, Amsinckia, Scarlet Pimpernel, Bugloss, Stinking Mayweed, Fool's Parsley, Orache, Black Mustard, Shepherd's Purse, Cornflower, Mouse-ear, Chickweed, Fat Hen, Goosefoot, All-seed, Corn Marigold, Creeping Thistle, Field bindweed, Bellbine, Wild Carrot, Larkspur, Horsetails, Common Storksbill, Treacle Mustard, Petty Spurge, Lesser Celandine, Fumitory, Hempnettle, Gallant Soldier, Cleavers, Dove's-foot, Cranes-fill, Henbit, Red Dead-nettle, Nipplewort, Venus's-looking-glass, Fluellens, Corn Cromwell, Wild Chamomile, Scentless Mayweed, Black Medick, White Campion, Corn Mint, Annual Mercury, Forget-me-not, Common Poppy, Greater Plantain, Ribwort, Knotgrass, Black Bindweed, Pale Persicaria, Redshank, Corn Crow foot, Corn Buttercup, Wild Radish, Broad-leaved Dock, Curled Dock, Groundsel, Charlock, Black Nightshade, Sow-Thistle, Spurrey, Common Chickweed, Pennycress, Scented Mayweed, Annual Nettle, Wall Speedwell, Ivy-leaved Speedwell, Common Field Speedwell, Vetch, Field Pansy, and the like.

The compositions of the present invention are particularly convenient for application to areas in which crops such as grain cereals, e.g. wheat, barley, oats and rye, sugar cane, onions, leeks, grasses, flax, forage legumes, and the like, will be grown or are in the course of growing. The amount of the final aqueous composition which is applied will vary accordingly to the nature of the weeds, the actual composition applied, the mode and time of application, and the presence of any crops. As a general rule from about 0.63 to about 2.8 kg of total active ingredient per hectare in cereal crops has been found to give good results. The concentrated formulations of the present invention thus are diluted to the desired final use rate of active ingredient.

The following examples will serve to further typify the nature of the invention without being a limitation on the scope thereof.

EXAMPLE 1

12.0 parts by weight of ®Ethylan CD916 (an alcohol ethoxylate) and 2.0 parts by weight of ®Tetronic 904 (an ethylene oxidepropylene oxide copolymer on to EDTA) were added to 44.8 parts by weight of Mecoprop acid, in the form of a potassium salt aqueous solution. Once the surfactants were dissolved, the solution was brought to pH 7.5 by the addition of approximately 1.3 parts by weight of commercially-available 65% xylene sulphonic acid solution (®Eltesol XA265). 5.6 parts by weight of Ioxynil as than octanoate ester and 5.6 parts by weight of Bromoxynil as the octanoate ester were then added and stirred until fully dissolved. 3.0 parts by weight of a naphthalinic solvent (®Solvesso 200) were added, stirred until dissolved, then made up with water to 100% by volume. Stirring was continued until a homogeneous product was obtained.

EXAMPLE 2A

Using the procedure described in Example 1, the following composition was formulated:
49.0 parts by weight of Mecoprop acid, in the form of a potassium salt solution,
7.0 parts by weight of Ioxynil, as the octanoate ester,
7.0 parts by weight of Bromoxynil, as the octanoate ester,
1.5 parts by weight of xylene sulphonic acid,
2.0 parts by weight of Ethylan ® CD916,
2.0 parts by weight of Tetronic ® 904,
5.0 parts by weight of Solvesso ® 200,
Water to 100% by volume.

The compositions of Examples 1 and 2A had the following characteristics:
Appearance: homogeneous liquids
Dilution in water: spontaneous emulsification to form a stable emulsion when tested according to CIPAC Test Method MT 36.
Stability: stable at ambient temperatures in the finished pack
Low temperature stability no crystallization occurs at temperatures above 0° C. when tested according to CIPAC Test Method MT 39.

EXAMPLE 2B

A formulation similar to that of Example 2A was prepared, omitting the Solvesso ® 200 naphthaline solvent. The composition of Example 2A remained clear until the ambient temperature was reduced to 0° C. The formulation of this Example deposited the ioxynil and bromoxynil components shortly after the temperature was reduced to below 20° C.

The following compositions of Examples 3 to 8 were formulation using the procedure described in Example 1:

EXAMPLE 3

| | |
|---|---|
| Mecoprop, in the form of the potassium salt solution | 448 g/liter |
| Ioxynil, in the form of the octanoate ester | 56 g/liter |
| Bromoxynil, in the form of the octanoate ester | 56 g/liter |
| Solvesso ® 200 | 30 g/liter |
| Dispersing Agent SS ® Liquid polymeric organic sulphonic acid sodium salt | 20 g/liter |
| Lactic acid, (50% technical) | approx. 35 g/liter |
| Tap water | to 100% by volume. |

EXAMPLE 4

| | |
|---|---|
| Mecoprop, in the form of the potassium salt solution | 448 g/liter |
| Ioxynil, in the form of the octanoate ester | 56 g/liter |
| Bromoxynil, in the form of the octanoate ester | 56 g/liter |
| Solvesso ® 200 | 30 g/liter |
| Soprophor ® FL neutralized phosphoric acid ester | 30 g/liter |
| Lactic acid, (50% technical) | approx. 30 g/liter |
| Tap water | to 100% by volume. |

EXAMPLE 5

| | |
|---|---|
| Mecoprop, in the form of the potassium salt solution | 480 g/liter |
| Ioxynil, in the form of the octanoate ester | 50 g/liter |
| Bromoxynil, in the form of the octanoate ester | 50 g/liter |
| Tetronic ® 904 | 30 g/liter |
| Ethylan CD ® 916 | 10 g/liter |
| Xylene sulphonic acid (65%) | approx. 20 g/liter |
| Xylene | 50 g/liter |
| Tap water | to 100% by volume. |

EXAMPLE 6

| | |
|---|---|
| Mecoprop, in the form of the potassium salt solution | 448 g/liter |
| Ioxynil, in the form of the octanoate ester | 56 g/liter |

-continued

| | |
|---|---|
| Bromoxynil, in the form of the octanoate ester | 56 g/liter |
| Tetronic ® 904 | 20 g/liter |
| Ethylan CD ® 916 | 20 g/liter |
| Xylene sulphonic acid (65%) | approx. 20 g/liter |
| Di-n-butyl phthalate | 40 g/liter |
| Tap water | to 100% by volume. |

EXAMPLE 7

| | |
|---|---|
| Mecoprop, in the form of the potassium salt solution | 448 g/liter |
| Ioxynil, in the form of the octanoate ester | 56 g/liter |
| Bromoxynil, in the form of the octanoate ester | 56 g/liter |
| Agrimul ® UE phosphoric acid ester | 40 g/liter |
| Xylene sulphonic acid (65%) | approx. 10 g/liter |
| Solvesso ® 200 | 50 g/liter |
| Tap water | to 100% by volume. |

EXAMPLE 8

| | |
|---|---|
| Mecoprop, in the form of the amine salt solution | 448 g/liter |
| Ioxynil, in the form of the octanoate ester | 10 g/liter |
| Bromoxynil, in the form of the octanoate ester | 10 g/liter |
| Tetronic ® 904 | 20 g/liter |
| Ethylan CD ® 916 | 20 g/liter |
| Xylene sulphonic acid (65%) | approx. 5 g/liter |
| Solvesso ® 200 | 20 g/liter |
| Tap water | to 100% by volume. |

EXAMPLE 9

| Ingredients: | |
|---|---|
| Isoproturon, in the form of HYTANE ® 500L ex CIBA-GEIGY | 300 g/liter |
| Mecoprop, in the form of the potassium salt solution | 203.6 g/liter |
| Bromoxynil, in the form of the octanoate ester | 30 g/liter |
| Dispersing Agent SS ® Liquid polymeric organic sulphonic acid sodium salt | 40 g/liter |
| Phospholan ® PNP-9 phosphoric acid ester | 20 g/liter |
| Xylene sulphonic acid (65%) | approx. 10 g/liter |
| Xylene | 5 g/liter |
| Tap water | to 100% by volume. |

Procedure

Completely dissolve the Dispersing Agent SS ® Liquid, xylene sulphonic and Phospholan ® PNP-9 in the Mecoprop salt solution. Add molten bromoxynil octanoate ester and xylene to this solution. Cool the solution to 20° C. and with constant agitation, add the HYTANE ® 500L until a homogeneous suspension is obtained. Make up to volume with tap water.

EXAMPLE 10

| Ingredients: | |
|---|---|
| Isoproturon, in the form of HYTANE ® 500L ex CIBA-GEIGY | 300 g/liter |
| Mecoprop, in the form of the potassium salt solution | 203.6 g/liter |

-continued

| Ingredients: | |
|---|---|
| Bromoxynil, in the form of the octanoate ester | 20 g/liter |
| Ioxynil, in the form of the octanoate ester | 7 g/liter |
| Phospholan ® PNP-9 phosphoric acid ester | 15 g/liter |
| Agrimul ® UE phosphoric acid ester | 25 g/liter |
| Dispersing Agent SS ® Liquid polymeric organic sulphonic acid sodium salt | 40 g/liter |
| Solvesso ® 200 | 5 g/liter |
| Tap water | to 100% by volume. |

Procedure

Completely dissolve the Dispersing Agent SS ® Liquid, Agrimul ® UE and Phospholan ® PNP-9 in the Mecoprop salt solution. Add molten bromoxynil and ioxynil octanoates and the Solvesso ® 200 to this solution. Cool the solution to 20° C. and with constant agitation, add the HYTANE ® 500L until a homogenous suspension is obtained. Make up to the indicated volume with tap water.

Examples 9 and 10 provide illustrations of concentrates of this invention containing a solid active ingredient (Hytane) which does not dissolve in the Mecoprop salt solution but remains suspended in it, thereby increasing the spectrum of biological activity of the concentrates of the invention.

EXAMPLE 11

| Ingredients: | |
|---|---|
| Isoproturon, in the form of HYTANE ® 500L ex CIBA-GEIGY | 300 g/liter |
| Mecoprop, in the form of the potassium salt solution | 203.6 g/liter |
| Bromoxynil, in the form of the octanoate ester | 13.6 g/liter |
| Ioxynil, in the form of the sodium salt | 28.6 g/liter |
| Phospholan ® PNP-9 phosphoric acid ester | 15 g/liter |
| Agrimul ® UE phosphoric acid ester | 25 g/liter |
| Dispersing Agent SS ® Liquid polymeric organic sulphonic acid sodium salt | 40 g/liter |
| Solvesso ® 200 | 10 g/liter |
| Tap water | to 100% by volume. |

Procedure

Completely dissolve the Dispersing Agent SS ® Liquid, ioxynil sodium salt, Agrimul ® UE and Phospholan ® PNP-9 in the Mecoprop salt solution. Add molten bromoxynil octanoate and Solvesso ® 200 to this solution. Cool the solution to 20° C. and with constant agitation, add the HYTANE ® 500L until a homogeneous suspension is obtained. Make up to the indicated volume with tap water.

EXAMPLE 12

56 grams of 2,6-diiodo-4-cyanophenol, in the form of the octanoate ester and 56 grams of 2,6-dibromo-4-cyanophenol, in the form of the octanoate ester, are added to a commercially-available solution of mecoprop, in the form of its potassium salt, to give a concentration of 550 g/l of mecoprop. The mixture is thoroughly stirred until a homogeneous clear liquid is obtained. The mixture is then made up to 1 liter using tap water and re-homogenized to form a homogeneous clear liquid.

EXAMPLE 13

Following the general procedure of Example 12, but reducing the amount of potassium 2-(4-chloro-2-methylphenoxy)propionate to 448 grams, formulations were prepared with the following additional components.

| Components | Formulations | | | |
|---|---|---|---|---|
| | A | B | C | D |
| Lactic Acid (50% solution) | 30 g | — | 30 g | 30 g |
| Solvesso ® 200 | — | 20 g | 20 g | — |
| Sodium salt of phenolsulphonic acid/formaldehyde concentrate condensate | — | — | — | 10 g |
| Water | q.s. to 1 liter | q.s. to 1 liter | q.s. to 1 liter | q.s. to 1 liter |

All formulations were homogeneous, clear, stable liquids similar to that in Example 12.

Examples 12 and 13 illustrate concentrates of the present invention which contain neither surfactant nor organic solvent.

What is claimed is:

1. An aqueous liquid concentrate which comprises at least two herbicides, said herbicides comprising
   (a) a first herbicide of low water solubility which herbicide is selected from the group consisting of
      (i) a 2,6-diiodo-4-cyanophenyl alkanoate having up to 12 carbon atoms in the alkanoate group;
      (ii) a 2,6-dibromo-4-cyanophenyl alkanoate having up to 12 carbon atoms in the alkanoate group; and
      (iii) a mixture of (i) and (ii); and
   (b) a second herbicide which is a salt of a carboxylic acid in which
      (i) the cation is selected from the group consisting of the sodium, potassium, ammonia, dimethylamine, diethylamine, monoethanolamine, diethanolamine, triethanolamine and morpholine cations, and
      (ii) the anion is selected from the group consisting of the 2,3,6-trichlorobenzoic acid; 3,6-dichloro-2-methoxybenzoic acid; 2,4-di chloro-phenoxyacetic acid; 2,4,5-trichloro Phenoxyacetic acid; 2-methyl-4-chlorophenoxy acetic acid; 2-(2-methyl-4-chlorophenoxy) propionic acid; 2-(2,4-dichlorophenoxyl)propionic acid; 2-(2,4,5-trichlorophenoxy) propionic acid; 4-(2-methyl-4-chlorophenoxy) butyric acid; and 4-(2,4-dichlorophenoxy)butyric acid anions;

said first herbicide being present in said concentrate in an amount which is herbicidally effective and at a concentration which exceeds the normal solubility of said first herbicide in water but being fully dissolved in an aqueous solution of from a threefold to a twelvefold excess, relative to the amount by weight of said first herbicide, of said second herbicide so as to produce a clear, stable, homogeneous concentrate of said first and second herbicides.

2. A liquid concentrate according to claim 1 wherein said alkanoate group of said first herbicide contains from 2 to 8 carbon atoms.

3. A liquid concentrate according to claim 1 wherein said alkanoate is the octanoate group.

4. A liquid concentrate according to claim 1 wherein the cation of said second herbicide is the sodium or potassium salt cation.

5. A liquid concentrate according to claim 1 wherein said second herbicide is present in from a 4 to 12 fold excess of said first herbicide.

6. A liquid concentrate according to claim 1 which further comprises from 1% to 10% by weight of said formulation of an aromatic solvent.

7. A liquid concentrate according to claim 1 which further comprises an amount of an acid sufficient to maintain the pH of the concentration from 7 to 8.

8. A liquid concentrate according to claim 1 which further comprises a non-ionic or anionic surfactant.

9. A liquid concentrate according to claim 1 wherein said second herbicide is the potassium salt of 2-(4-chloro-2-methylphenoxy)propionic acid which salt is present in from a 4 to 12 fold excess of said first herbicide.

10. A liquid concentrate according to claim 1 wherein a third herbicide is present which does not dissolve in the solution of the second herbicide.

* * * * *